United States Patent [19]

Lisak et al.

[11] Patent Number: 5,524,640
[45] Date of Patent: Jun. 11, 1996

[54] INFANT POSITIONING DEVICE

[75] Inventors: Stephen P. Lisak; Larry L. Young, both of Arab; Sally B. Whitley, Birmingham, all of Ala.

[73] Assignees: Ryder International Corporation and Research Foundation, Arab; The University of Alabama at Birmingham Research Foundation, Birmingham, both of Ala.

[21] Appl. No.: 295,250

[22] Filed: Aug. 24, 1994

[51] Int. Cl.[6] .............................. A61F 5/37; A47C 27/00; A47C 20/02
[52] U.S. Cl. ...................... 128/846; 128/869; 5/655; 5/657
[58] Field of Search ................................. 5/603, 922, 640, 5/655, 657, 465, 41, 632, 636, 637; 128/845, 846, 869, 870, 875

[56] References Cited

U.S. PATENT DOCUMENTS

| | | | |
|---|---|---|---|
| 2,646,735 | 7/1953 | Brunnen | 5/655 |
| 3,306,287 | 2/1967 | Arp | 128/870 |
| 3,742,528 | 7/1973 | Münch | 5/465 |
| 3,877,093 | 4/1975 | Gershbein | 5/465 |
| 4,108,168 | 8/1978 | Craig | 128/870 |
| 4,977,630 | 12/1990 | Oswalt | 5/655 |
| 5,329,934 | 7/1994 | Bowman | 128/870 |
| 5,334,133 | 8/1994 | Carroll | 128/870 |

OTHER PUBLICATIONS

Developmental Intervention in the Newborn Intensive Care Unit, NAACOG Clinical Issues, pp. 84–110, 1991.

*Primary Examiner*—Michael A. Brown
*Attorney, Agent, or Firm*—Trexler, Bushnell, Giangiorgi & Blackstone, Ltd.

[57] ABSTRACT

An infant supporting and positioning system for retaining and supporting an infant in a selected position. The supporting and positioning system includes a generally horizontally oriented base which has a primary surface in which is formed a plurality of bores. The system includes a plurality of infant positioning modules each of which have a body portion and at least one post projecting from the body portion. The posts are sized and dimensioned for cooperative engagement with a corresponding one of the plurality of the bores in the base. The posts interfit with the bores with sufficient interference to maintain the modules in the selected position relative to the base. The interference between the posts and bores allow for removal of a post from a bore to change the position of the corresponding module as necessary to configure the system to achieve desired infant support and positioning. The infant support and positioning system is generally covered with a vapor barrier and padded layer to provide additional protection and comfort.

17 Claims, 4 Drawing Sheets

INFANT POSITIONING DEVICE

BACKGROUND

The present invention relates to devices for supporting and positioning infants. More specifically, the present invention is for use by premature or ill infants, who may have special developmental requirements which can be improved through proper support and positioning.

Improvements in medical technology have been increasing the overall survival rate of prematurely born infants or infants born with medical complications. While general medical technology has provided the means to help the infants survive, such infants still encounter developmental problems which occur as a result of their delicate condition. Their developmental problems may be exacerbated by the prolonged period of time which they may spend in the intensive care unit of a hospital.

More particularly, premature and critically ill infants, or developmentally challenged infants, experience developmental problems since they are not prepared to handle the stimuli of the extravitro world as a result of their young gestational age, health status or other developmental limitation. It is extremely important to provide a developmentally appropriate environment for such infants to enhance development and limit further complications which may be brought on by developmental deficiencies.

Recent studies, such as *Developmental Intervention in the Newborn Intensive Care Unit* by Ms. Sally Whitley (a co-inventor of the present invention) NAACOG's Clinical Issues, p. 84–110, 1991, emphasize the effects of the newborn intensive care unit (NICU) environment on newborns. This study indicates that the first goal of a developmental intervention program for NICU patients is to modify the intensive care unit environment to reduce detrimental stimuli to the lowest possible level in order to promote homeostasis. Modification of the NICU environment helps the infants to regulate their physiological and behavioral functioning. Basic and critical components of the environmental modification include providing proper support and positioning of the infant and minimization of stress. When an infant's body is properly supported and the overall environmental stress level is reduced, the infants can properly rest thereby promoting healthful development. If infants do not receive the necessary rest environmental stresses and bodily discomfort can slow the infant's development and possibly cause long-term harm.

Attempts have been made to create devices to support and position infants. A primary goal of infant positioning and supporting devices is to maintain proper body alignment in the prone, supine and side lying positions. The prior attempts at support and positioning infants have not been able to fully accommodate each of the basic infant positions. Further, prior art devices are not easily adjustable to accommodate each infant's initial condition as well as the infant's development based on age, size and condition.

Premature and critically ill infants are subject to skeletal and muscular problems since they often lack sufficient muscular and skeletal development to overcome gravitational forces. This condition, known as hypotonia, may contribute to postures in which the shoulders, hips, arms and legs fall away from the midline of the body. Hypotonia often results in unnatural muscle development and undesirable rotation of bodily joints. As a result, infants suffering from hypotonia may develop irregular structural support and posture.

Another problem that arises due to hypotonia is that the infant may develop behavioral insecurities. Newborn infants typically enjoy, and in fact need, a swaddled or enclosed space in which they are cradled and securely held. This position provides a degree of psychological stability and comfort as the infants make the transition from the womb to the outside world. When infants are hypotonic, they lack the ability to draw their limbs inwardly to achieve this swaddled or fetal position. This problem is exacerbated when infants are prematurely born since the fetal position would be an essential posture if they were still developing in the womb.

Attempts have been made to provide support for hypotonic infants to prevent or reverse the detrimental physical and behavioral development discussed hereinabove. Prior attempts have included positioning these infants on off-the-shelf devices, often designed for other purposes, to provide the necessary support and positioning. Such devices have included water beds, inflatable mattresses and pads, bean bags, gel-foam structures, "egg crate" foam mattress material, sheepskin, rolled linens and diapers, and even infant car seats and carriers. None of the previous attempts have fully satisfied the needs of developmentally challenged infants.

Other problems may arise in addition to hypotonia such as skeletal damage as a result of the premature infant having very fragile malleable limbs. If the limbs are not properly directed in their development, the limbs may take on permanent abnormalities or deformities which could result in structural and physical complications throughout life. Early intervention in supporting and positioning the infant while in the NICU can prevent the need for long-term and expensive physical therapy and physical implements such as splints or surgery to correct abnormalities which develop.

Another problem that arises with premature infants is that their heads tend to develop flattened areas or become elongated. This problem is a result of the immature bone structures in the skull being deformed when the premature infant does not actively or readily change their head position. In an attempt to overcome the flattening problems, soft toroids or "donuts" have been produced. Not all infants are able to tolerate the donuts either as a matter of comfort, or as a matter of the shape of their head, size of their head or any other special requirements. As an additional matter, these donuts tend to position the infant's head out of alignment relative to the rest of the body thereby adding another variable in the alignment and posture problem described hereinabove.

A developmentally challenged infant needs to be positioned and supported by a system which can be configured for his specific needs. The positioning and support system also must be able to be reconfigured as the infant grows or as his needs change so that the support and positioning is always appropriate for his stage of his development or status of his condition. Further, the system must be standardized such that hospital personnel, and even parents can use the system in a predictable manner without complications. It is important for an infant positioning and support system to help reduce or eliminate other environmental stresses such as heat dissipation and to minimize the interference with the infant when the system needs to be reconfigured.

Most of the prior art attempts to overcome the infant positioning and support problems discussed hereinabove introduced or failed to eliminate some form of environmental stress thereby making the device infeasible. For example, the water filled and air filled bags, while providing a degree of support, introduced heat dissipation problems. Heat dissipation is an environmental stress which is highly detrimental to a developmentally challenged infant. It is important, and often critical, to the infant's stability to maintain temperature homeostasis. The water filled bags tend to dissipate heat rapidly thereby decreasing the temperature of the infant and introducing environmental stress. While a heating device may be used in conjunction with the water filled bag, heating devices introduce another variable which must be monitored and controlled. Such heating devices are subject to overheating, underheating, failure to heat, as well as increasing the cost and complexity of the system.

Additionally, prior art devices are often cost prohibitive or required trial and error fitting for each infant and for each configuration for a specific infant. The devices are cost prohibitive because they must be configured and customized for each child. In essence, the prior art devices are often a matter of "redesigning the wheel" for each infant. By redeveloping the positioning and support system for each infant not only is the material cost increased but professional health care provider time is spent thereby substantially increasing the overall cost.

With regard to the problems of trial and error fitting, numerous devices have been designed to satisfy the specific requirements of an individual infant. For example, taped linens and sheepskin rolls may be customized for each child but are difficult to reconfigure, requiring adjustment of the roll size and retaping. Further, the rolled devices required another structure to retain the rolls in the desired supporting desired position. The supporting devices used to wedge the rolls in place introduced yet additional variables and possible failure point in the supporting system.

The prior art devices do not overcome the problems encountered in positioning and supporting developmentally challenged infants. It should be noted that the problems discussed hereinabove are further exacerbated when infants are sedated or otherwise chemically treated such as may be found in postoperative settings. The hypotonia discussed above is magnified by sedatives and these sedated infants may have no muscle tone and therefore are completely exposed to the detrimental effects of gravity.

OBJECTS AND SUMMARY

A general object of the present invention is to provide an infant supporting and positioning system which promotes development and minimizes environmental stresses.

Another object of the present invention is to provide an infant supporting and positioning system which includes standardized support and positioning modules which are configurable to the specific requirements of individual infants.

Yet another object of the present invention is to provide an infant supporting and positioning system which is easy to use and inexpensive.

Briefly, and in accordance with the foregoing, the present invention envisions an infant supporting and positioning system for maintaining an infant in a selected position and providing specifically configured support. The supporting and positioning system includes a generally horizontally oriented base which has a primary surface in which is formed a plurality of bores. The system includes a plurality of infant positioning modules each of which have a body portion and at least one post projecting from the body portion. The posts are sized and dimensioned for cooperative engagement with a corresponding one of the plurality of bores in the base. The posts interfit with the bores with sufficient interference to maintain the modules in the selected position. The interference between the posts and bores allow for removal of a post from a bore to change the position of the corresponding module as necessary to achieve desired infant support and positioning. The infant support and positioning system is generally covered with a vapor barrier and padded layer to provide additional protection and comfort.

BRIEF DESCRIPTION OF THE DRAWINGS

The organization and manner of the structure and operation of the invention, together with further objects and advantages thereof, may be understood by reference to the following description taken in connection with the accompanying drawings, wherein like reference numerals identify like elements, and in which.

DETAILED DESCRIPTION OF THE PREFERRED EMBODIMENT

Figure 1:
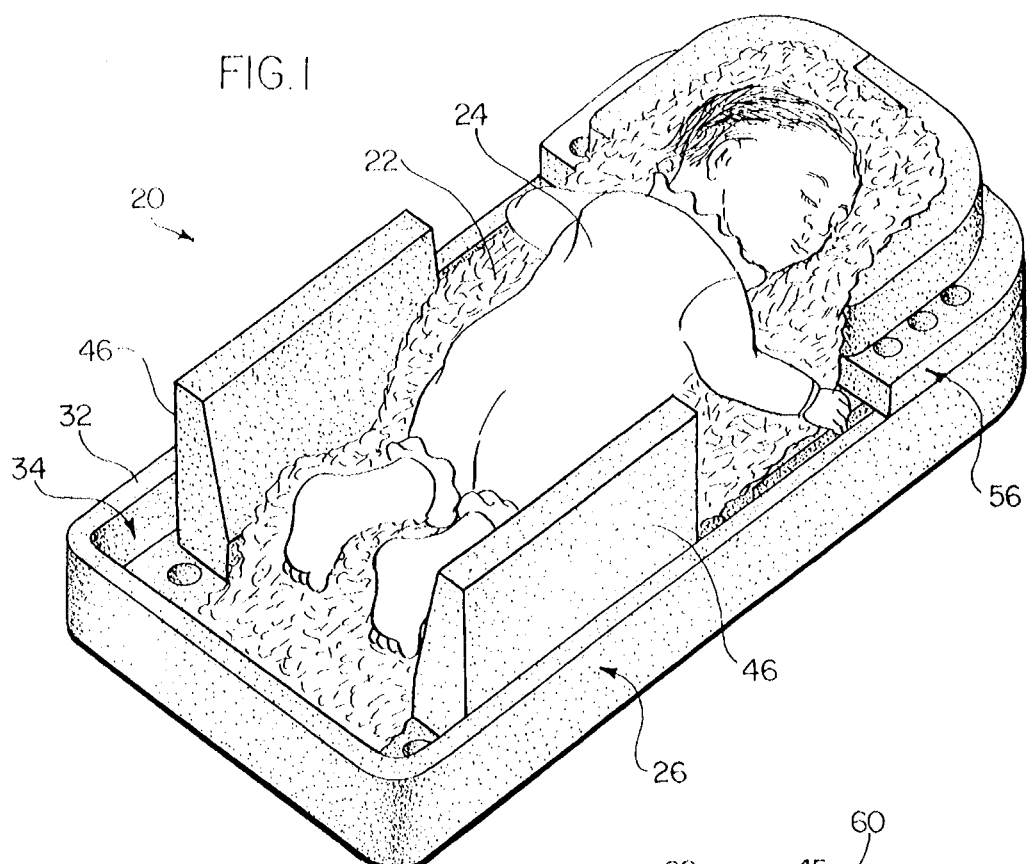
FIG. 1 is a perspective view showing an infant lying in a prone position on an infant supporting and positioning system of the present invention in which the infant is lying on bedding material, such as sheepskin, blanketing the structure of the system.

While the invention may be susceptible to embodiment in different forms, there is shown in the drawings, and herein will be described in detail, an embodiment with the under-standing that the present description is to be considered an exemplification of the principles of the invention and is not intended to limit the invention to that as illustrated and described herein.

Figure 2:
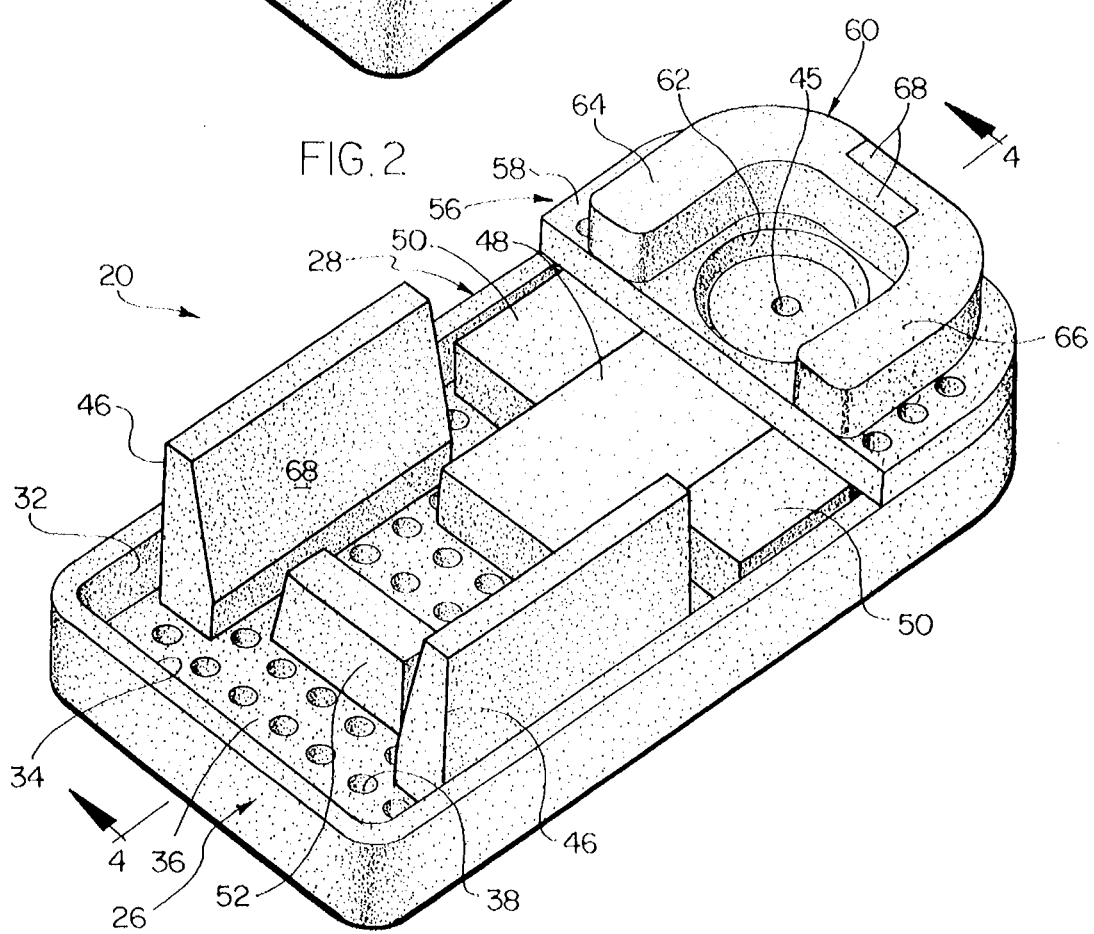
FIG. 2 is a perspective view of the infant support and positioning system as shown in FIG. 1 in which the infant and bedding material have been removed to show a plurality of infant positioning modules retained on a base.

With reference to FIG. 1, an infant supporting and positioning system 20 in accordance with the present invention is shown with a bedding material 22 blanketing the structure of the positioning system 20 and an infant 24 lying on top of the bedding 22. FIG. 2 shows the system 20 as shown in FIG. 1 with the bedding 22 and infant 24 removed.

Figure 5:
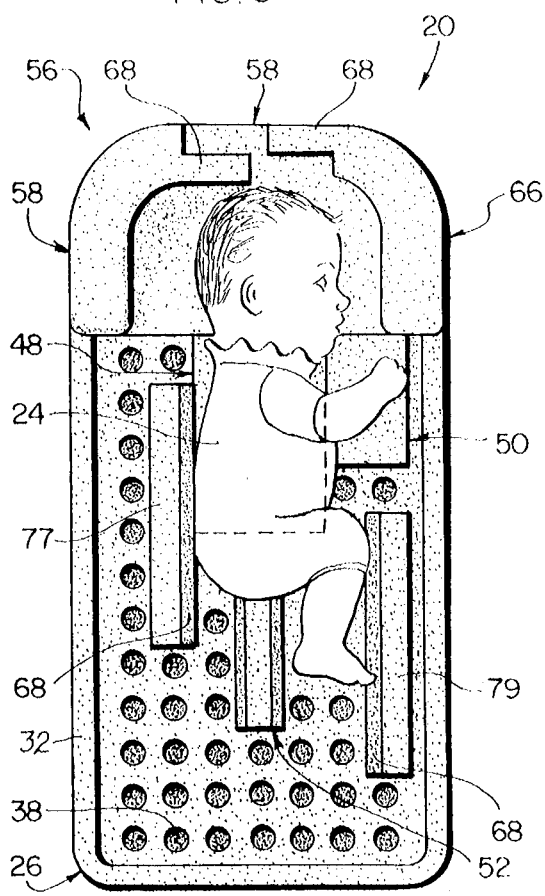
FIG. 5 is a top plan view of the infant positioning and support system configured for supporting an infant in a side lying position.
Figure 6:
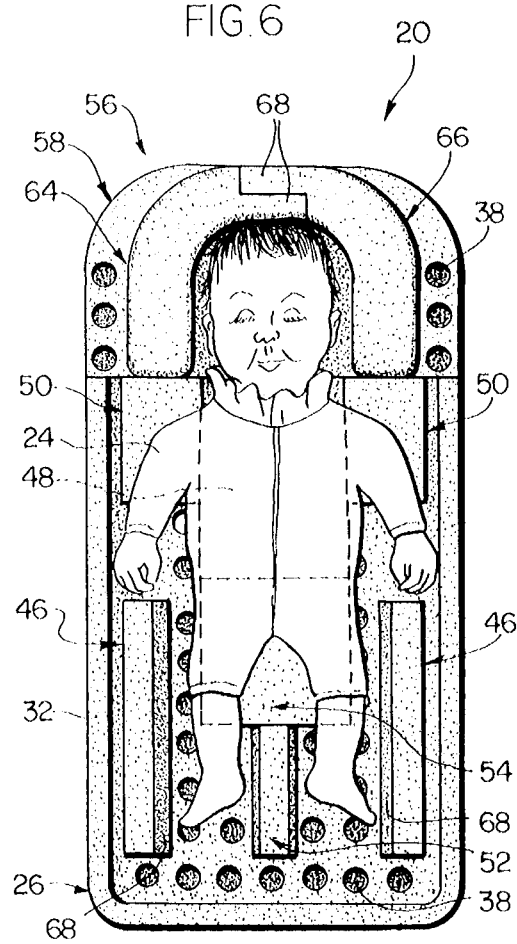
FIG. 6 is a top plan view showing the infant positioning and support system configured for supporting an infant in a supine position.

The system can be configured as shown in FIG. 1 to provide support in a prone lying position, while FIG. 5 shows a configuration to provide support in a side lying position, and FIG. 6 shows configuration to provide support for a supine position. In FIGS. 5 and 6, the bedding material has been removed to more clearly show the relationship between the system and the position of the infant placed thereon.

Figure 3:
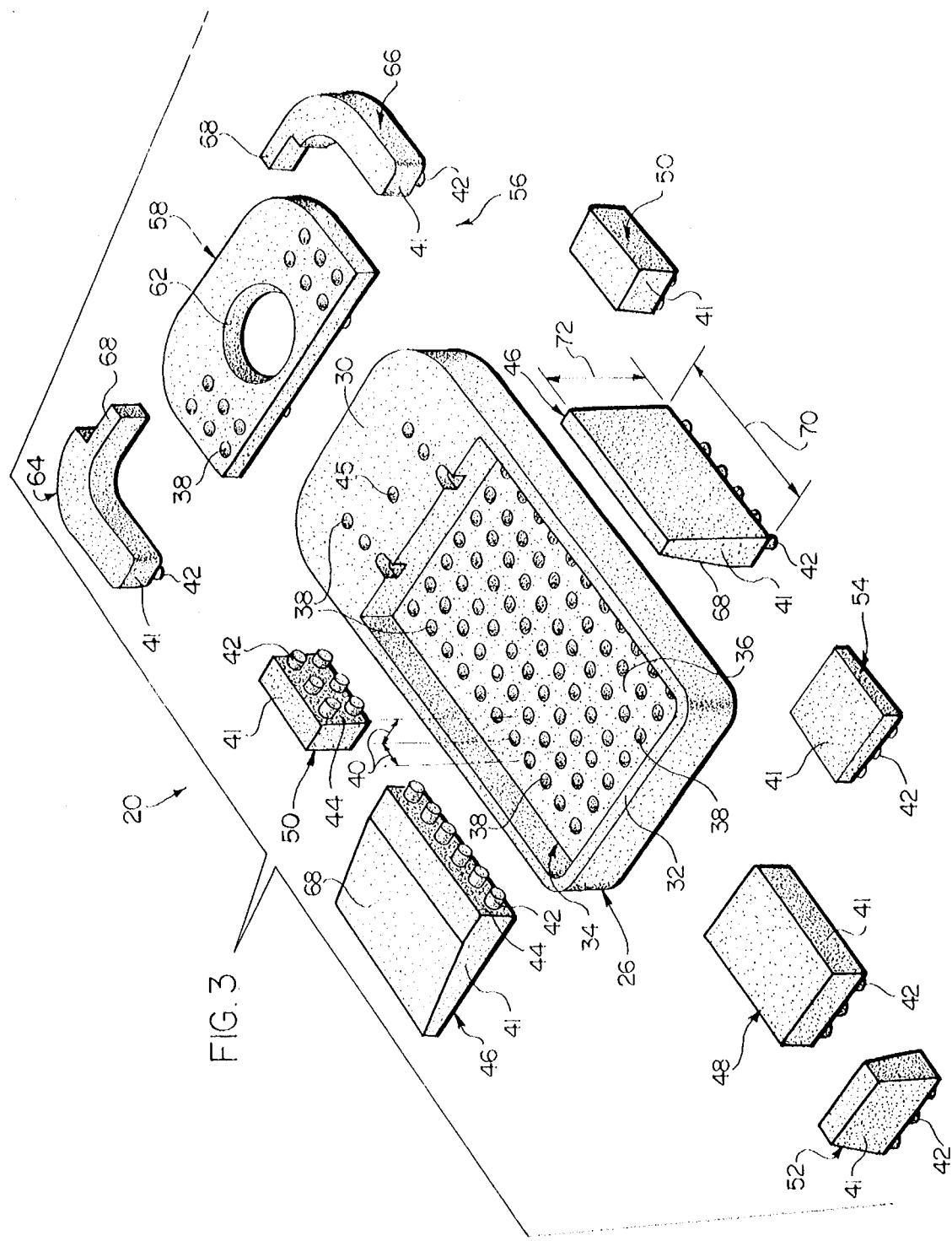
FIG. 3 is an exploded perspective view of the infant positioning and support system showing the positioning modules exploded away from a base portion and peg and bore structures associated with the modules and base, respectively.
Figure 4:
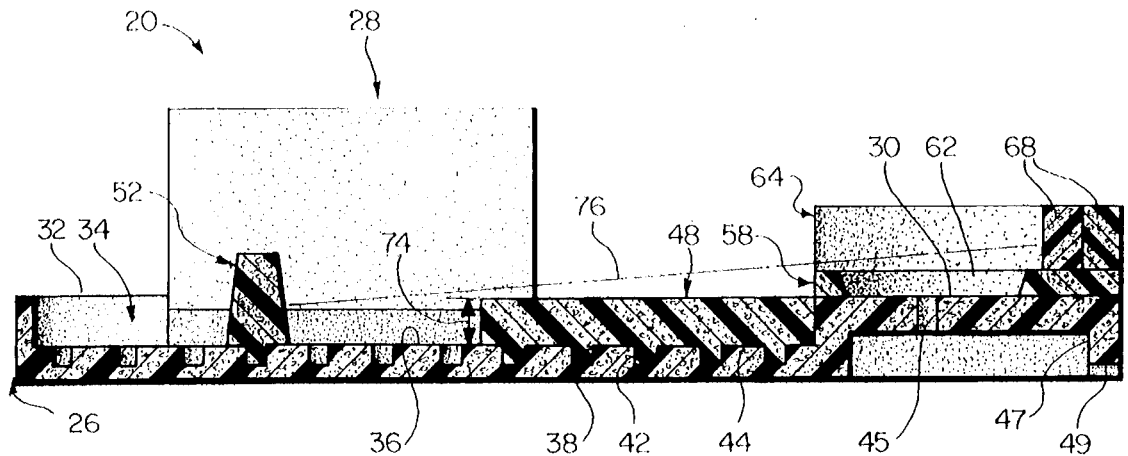
FIG. 4 is a partial fragmentary, cross-sectional, side-elevational view taken along line 4—4 in FIG. 2 showing the engagement of the posts extending from the modules into the bores in the base.

The positioning system 20 as shown in FIG. 2 and as further shown in the exploded perspective view of FIG. 3 includes a base 26 and a plurality of infant positioning modules 28 cooperatively engaged with the base 26. With reference to FIGS. 2, 3 and 4, the base 26 includes an elevated head portion 30 and an extending rim 32 defining a recessed area 34. A primary surface or mounting surface 36 is positioned in the bottom of the recessed area 34 and has a plurality of bores 38 formed therein.

Each module 28 has a body portion 41 and includes at least one post 42 extending from a bottom surface 44 of the body 41. As more clearly shown in FIG. 4, each post 42 is cooperatively engageable with a corresponding bore 38 producing an interference fit to retain the module 28 in position relative to the primary surface 36. The modules 28 include, but are not limited to, lateral support modules 46, an upper torso module 48, arm support modules 50, a leg or foot support module 52 and a lower torso module 54. While the modules as shown in FIG. 3 are rather rectilinear, the corner edges of the modules can be curved or radiused to provide a more rounded arcuate surface. Additionally, the surfaces of the modules can be formed with concave or convex surfaces in order to accommodate various desired posture configurations. For example, the upper torso module 48 may be formed with a concave surface to more specifically receive and cradle the upper torso of an infant. Additionally, the arm support modules may be formed with a concave arcuate surface to support the arms of an infant.

The bores 38 are arranged in the mounting surface 36 with each bore positioned at equidistant spaced intervals in a grid pattern. The posts 42 are similarly positioned. The posts 42 and bores 38 are spaced on a rectilinear grid pattern so that the modules may be moved at incremental distances defined by the dimensions of the intervals 40. As such, when an infant grows or otherwise requires additional space, a module which must be moved as a result of this change can be moved a predictable increment. This is in contrast to the prior art which provided no predefined increments or intervals for positioning support devices such as rolled linens and the like.

Figure 4A:
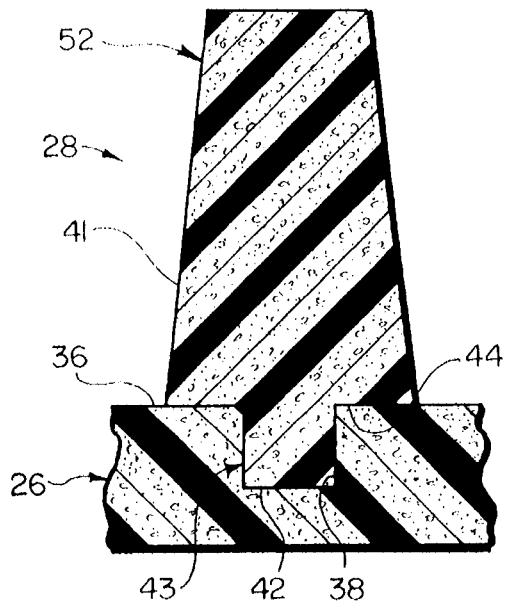
FIG. 4a is an enlarged partial fragmentary, cross-sectional side-elevational view of a foot support module as shown in FIG. 4 showing a post structure integrally formed with a body portion of the foot support module and engagement of the post with a corresponding bore.
Figure 4B:
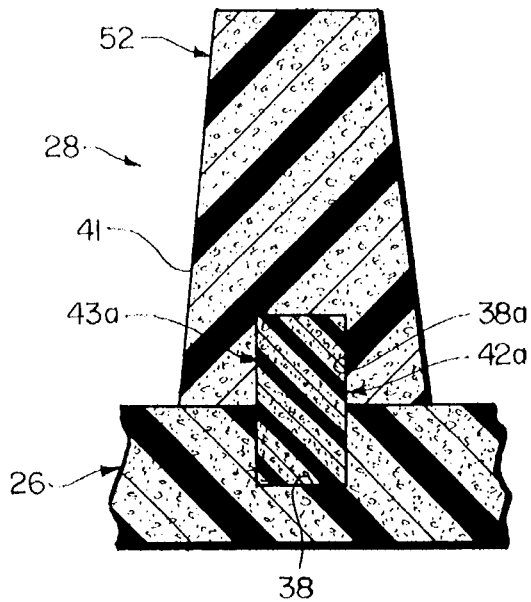
FIG. 4b is an enlarged partial fragmentary, cross-sectional side-elevational view of a module which is similar to the foot support module as shown in FIG. 4 in which the post is an independent component engageable with the body of the foot support module and a corresponding bore.
Figure 4C:
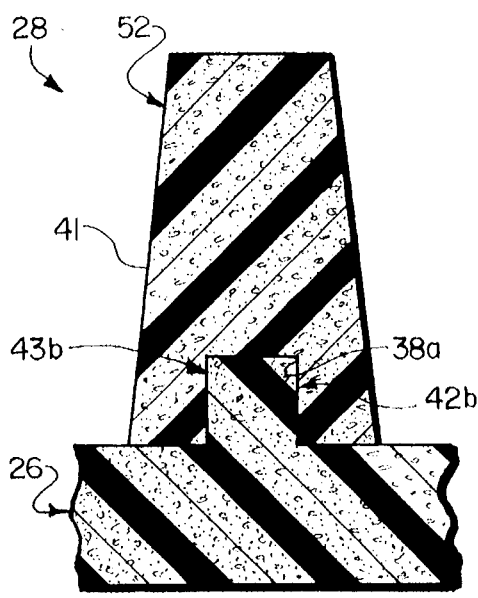
FIG. 4c is an enlarged partial fragmentary, cross-sectional side-elevational view of a module which is similar to the foot support module as shown in FIG. 4 in which a post is integrally formed with the base for engagement in a corresponding bore formed in the body portion of the foot support.

FIGS. 4a, 4b and 4c provide an enlarged partial fragmentary, cross-sectional side-elevational views showing a variety of configurations for engaging a module 28 with the base 26. For example, FIG. 4a shows engagement means 43 which includes the post 42 cooperatively engaged with a bore 38 formed in the base 26. The post 42 of the engagement means 43 is integrally formed with the body 41 of the foot support module 52.

FIG. 4b shows engagement means 43a which includes a post 42a which is an independent component and is engageable with a bore 38 formed in the base 26 and a bore 38a formed in the body 41 of the foot support module 52. The embodiment as shown in FIG. 4b allows the post to be used independently of the module 28 and the base 26. The benefit of such a post is that if a post becomes damaged or broken, the post can be discarded without having to discard the entire module as a result of a damaged post.

FIG. 4c shows engagement means 43b which includes a post 42b integrally formed with the base 26 for engagement with a bore 38a formed in the body portion 41 of the foot support module 52.

The infant positioning modules 28 also include a multi-component head positioning module assembly 56. The head positioning assembly 56 includes a skull support module 58 which is engageable with the elevated portion 30 and a head positioning collar 60 attachable to the skull support module 58 using the post and bore structures. A recess 62 is formed in the skull support module 58 to circumferentially support an infant's head as will be discussed hereinbelow. The positioning collar 60 includes first and second arcuate portions 64, 66, respectively, each portion 64,66 having an interfitting extension 68. Posts 42 are provided on the bottom side of the positioning collar 60 as well as the skull support module 58 for cooperative engagement in a desired infant positioning and supporting configuration.

Figure 3A:
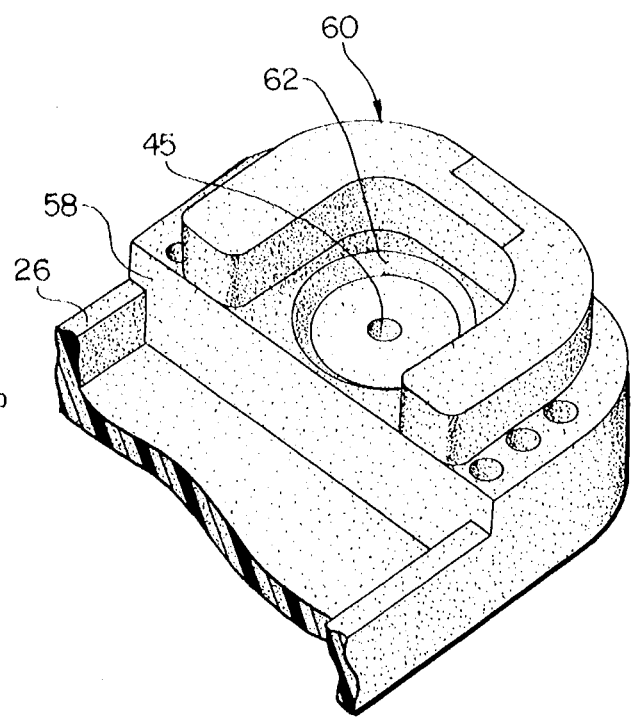
FIG. 3a is a partial fragmentary, perspective view of a portion of the base showing a skull supporting portion integrally formed with the base.

With reference to FIG. 3a, the skull support module 58 is integrally formed with the base 26 to reduce the number of separate pieces in the system 20. The positioning collar 60 is attachable to the skull support module as described hereinabove. Additionally, a breathing hole 45 is formed through the skull support module 58 and the base 26. The breathing hole 45 is formed through the skull support module 58 generally in the area of the recess 62. The breathing hole 45 helps to maintain the infant's supply of air even if an infant rolls over and lies face down in the recessed area 62. The breathing hole 45 is also shown in FIGS. 2, 3 and in a cross-sectional view as shown in FIG. 4. With further reference to FIG. 4, a hollowed area 47 has been formed underneath the skull support module 58 to maintain a uniform wall thickness and to provide an air space when an infant breathes through the breathing hole 45. Additionally, an air passage 49 is formed to connect the hollowed area 47 with the ambient atmosphere.

Lateral support modules 46 are provided with a sloped surface 68 to allow ease of placement of an infant between opposedly positioned lateral support modules 46, 46. The lateral support modules 46 are elongated (as indicated by dimension arrow 70) to provide consistent support and positioning along the length of the infant to maintain proper primary alignment of the infant's body components. For example, as shown in FIGS. 1 and 6, the lateral supports 46 are positioned to retain the infant's legs in proper alignment with the shoulders and hips. Such positioning provides the beneficial effect of preventing misalignment of the joints and promoting proper muscle development.

The lateral supports 46 also have a rather tall vertical dimension (as indicated by dimension arrow 72) compared to the other modules. The increased vertical dimension 72 prevents the infant from kicking his legs over the top of the lateral support 46 should the infant thrash or raise his legs. It is a common action for infants to raise their legs towards their chest. As such, the increased vertical dimension 72 prevents an infant from throwing his leg over the side of the lateral support 46 and maintains the proper alignment even if an infant brings his legs towards his chest. Another important benefit to the length and height 70, 72, respectively, of the lateral supports 46 is the psychological benefit of the feeling of being enclosed or swaddled and increased tactile stimulation. The infant is limited in his side to side movement and therefore the modules define the limitations of the infant's environment to provide psychological security.

Supporting and positioning features are provided for the infant's head by the head positioning module assembly 56. The curved shape of the recess 62 in the skull support module 58 bears the weight of the infant's head through the back and the circumferential surface of the head rather than merely one side. This is an important feature since failure to circumferentially support an infant's head may result in a flattening and elongation of the head. By receiving the convex shape of the infant's skull in the concave curved shape of the recess 62, the skull will develop in a curved shape as opposed to a flattened shape as the skull structures ossify. While the flattening and elongation of an infant's head may not affect the infant's brain, this type of deformity may have a psychological effect on the infant as well as the parents. Therefore, the elimination of the flattened skull which often occurs in premature infants is a very important solution to a long standing problem.

The positioning collar 60 provides boundaries to the infant's environment and maintains the head in alignment with the shoulders and the hips thereby promoting proper postural development. The collar 60 allows the infant to move his head from side to side while in an aligned position. Additionally, the collar 60 can be positioned with the interfitting extensions 68 engaged (as shown in FIGS. 1, 2 and 6) or with the collar spread apart (as shown in FIG. 5) to provide a wider opening between the first and second portions 64, 66. The wider opening may be necessary as an infant grows or if medical devices, such as ventilation hoods, are placed near or next to the infant's head. The configuration flexibility of the invention easily accommodates many situations.

The upper torso module 48, lower torso module 54, arm modules 50, and leg support 52 can be arranged as shown in FIGS. 2, 5 and 6 to provide bodily support for a variety of configurations. For example, in FIG. 2, these components 48, 50 and 52 are arranged to support the infant's torso and arms as well as to flex the infant's legs. The leg support 52 is positioned under the infant's ankles so that the legs are flexed at the knee thereby promoting proper muscular and skeletal development. With reference to FIG. 4, the upper torso support 48 is formed with a height dimension 74 to provide support at an elevation greater than the surface of the primary surface 36 yet lower than the upper surface of the panel 58. In other words, as shown in FIG. 4, the components may be configured to provide a gently upwardly sloped (as indicated by fall line 76) to support the infant in a position with a slightly elevated head. The slight elevation may be beneficial to the infant's body functions such as digestion and breathing.

With further reference to FIG. 4, the skull support module 58 is positioned to allow the curve of the infant's skull to fit in the recess 62 while maintaining the infant in the inclined position along the fall line 76. This is an important contrast to the prior art such that the prior art "donuts" as discussed hereinabove, tended to raise the infant's head out of alignment relative to the rest of the infant's body.

In FIG. 5, the system has been configured with an upper torso module 48 to support the infant on its side with the leg support 52 vertically aligned on the primary surface providing posterior support. The lateral support modules 46 are positioned with a first module 77 providing spinal alignment and support and a second module 79 offset from the first module 77 restricting the movement of the legs. The infant is swaddled or restrictively supported between the lateral supports 77, 79 on either side and between the cradling collar 60 at the top and the leg support 52 at the bottom. This configuration also helps to maximize the tactile contact with the bedding material providing important sensory stimuli to add in the physical and behavioral development of the infant.

With reference to FIG. 6, the configuration shown herein is similar to that as shown in FIG. 2 except that a lower torso positioning module 54 is positioned underneath the buttocks of the infant and the leg support 52 is vertically aligned with the lateral support modules 46. This arrangement allows the infant to move his legs from side to side as well up to his chest and back. Also, the leg support 52 may be oriented so that it is positioned behind the infant's knees to flex the knees to aid in proper development. This is yet another example of the versatility of the present invention to accommodate specific needs of individual infants.

A shape retaining pliable soft foam material or a rigid foam is preferred for forming the modules 28 as well as the base 26. The foam material allows the system 20 to be formed using standardized molds or dies at low cost. In fact, the cost of producing such a system 20 using a foam material may make it economically feasible to consider the system 20 a disposable item. The low cost of production and standardization of the system helps make it feasible to send such systems home with newborns needing the support and positioning the system offers. It should also be noted that the modules 28 and the base 26 of the system 20 may be formed with hollow areas, such as is shown in FIG. 4, to maintain a uniform wall thickness thereby minimizing materials and improving the surface quality of the as-formed foam material. The recessed or hollowed areas are generally formed on a surface or side of the component which faces away from the infant.

As additional benefits, the foam components are formed without sharp edges and are light weight. In special circumstances, the characteristics of the foam material allow the modules to be custom carved. The foam provides an insulation effect which substantially reduces the heat dissipation from the infant. By eliminating or reducing the rate of heat dissipation from the infant, yet a further environmental stress is removed from the infant thereby promoting healthful development.

All of the above described characteristics of the infant positioning and supporting system 20 provide an optimal developmental environment for developmentally challenged infants. The system provides proper support and positioning of the infant's body, provides a comforting swaddling effect, prevents deformation of the head such as flattening and/or elongation, reduces environmental stresses, and allows the infant to be moved or transported without removing the infant from the system.

In use, the system 20 of the present invention is configured for a specific infant by positioning the base 26 in an appropriate location such as on a bed or in a bassinet, or crib. The system 20 is configured for the infant by positioning the modules 46 in the necessary location based on the desired infant positioning and the size of the infant. The modules are retained in the recessed area 34 of the base 26 by engaging the posts 42 projecting from the bottom surface 44 of the body of each module 46 with the bores 38 in the primary surface 36. Once the system has been configured for the infant, a bedding material or bed liner such as sheepskin is placed over the system 20 thereby providing additional warmth and tactile comfort as well as smoothing out the surfaces and edges of the modules mounted on the base.

The present invention provides a standardized system which can be custom configured for a specific infant in a specific position. Several systems can be provided for each infant and configured for a specific position such that when it is necessary to change the infant's position, the infant is merely lifted from one positioning configuration and placed into another configuration. For example, three systems could be provided configured for the prone, side-lying and supine positions as shown in FIGS. 1, 5 and 6. Then, when the infant needs to be moved from the prone position to the side lying position, the infant is merely lifted from the configuration as shown in FIG. 1 and placed in the configuration as shown in FIG. 5.

While a preferred embodiment of the present invention is shown and described, it is envisioned that those skilled in the art may devise various modifications of the present invention without departing from the spirit and scope of the appended claims. The invention is not intended to be limited by the foregoing disclosure.

The invention claimed is:

1. An infant supporting and positioning system for supporting an infant in a selected position, said infant positioning system comprising:

a base;

a plurality of infant supporting and positioning modules, each of said plurality of modules having a body portion positioned against and extending away from said base for aiding in the positioning of an infant said plurality of modules including at least; a pair of upstanding lateral support modules and an independent leg support module;

engagement means operatively associated with said base and said body of each of said lateral support modules and said independent leg support module, said engaging means retaining each of said modules in a selected position relative to said base to provide support and restraints for supporting an infant in a desired position, said engagement means includes a plurality of bores formed in at least one of said body of each of said modules and said base, at least one post operatively coupled with at least one of said bores and operatively coupled with one of said body and said base such that each of said modules are attached to said base by engaging said post in said bores at selected positions relative to said base in a configuration to provide support and restraints for supporting an infant in a desired position; and whereby said lateral support modules are generally positionable on said base with said leg support being positioned generally perpendicularly between said lateral supports for supporting the ankles of an infant when lying in a prone position and for supporting the knees of an infant in a supine position, and each of said plurality of modules being independently, selectively attached to said base for accommodating a variety of infant positions.

2. An infant supporting and positioning system as recited in claim 1, wherein said bores are formed in said base and said posts are integrally formed with and project from a corresponding side of said body of said module.

3. An infant supporting and positioning system as recited in claim 2, further comprising said bores in said base being arranged with each bore positioned at equidistant spaced intervals.

4. An infant supporting and positioning system as recited in claim 2, wherein said bores and said posts on said modules being generally equidistantly spaced in a rectilinear grid pattern, said posts on said modules being spaced apart consistent with the spacing of said bores for cooperative interfitting of said posts in said bores.

5. An infant supporting and system as recited in claim 1, wherein said bores are formed in said body of said module and said post are integrally formed with and project from a corresponding surface of said base.

6. An infant supporting and positioning system as recited in claim 1, wherein said lateral support modules are elongated and have a vertical dimension, measured relative to said base, which is greater than the other modules for generally preventing an infant from moving over a top edge thereof.

7. An infant supporting and positioning system as recited in claim 1, said plurality of infant supporting and positioning modules further comprising a torso support for supporting a portion of the torso of an infant positioned in said supporting and positioning system.

8. An infant supporting and positioning system as recited in claim 7, said plurality of infant supporting and positioning modules further comprising a pair of arm supports, and wherein said base, said torso support, and said pair of arm supports are sized and dimensioned for facilitating attachment of said torso support to said base with said arm supports being assembled to said base outboardly of said torso support.

9. An infant supporting and positioning system for supporting an infant in a selected position, said infant positioning system comprising:

a base;

a plurality of infant supporting and positioning modules, each of said plurality of modules having a body portion positioned against and extending away from said base for aiding in the positioning of an infant; and engagement means operatively associated with said base and said body of said module, said engaging means retaining said module in a selected position relative to said base to provide support and restraints for supporting an infant in a desired position, said bores being formed in both said body of said modules and said base, said post being an independent component sized and dimensioned for engaging cooperatively positioned bores of said body and said base for retaining said body engaged therewith relative to said base.

10. An infant supporting and positioning system as recited in claim 9, further comprising said bores in said base being arranged with each bore positioned at equidistant spaced intervals.

11. An infant supporting and positioning system as recited in claim 9, wherein said bores and said posts on said modules being generally equidistantly spaced in a rectilinear grid pattern, said posts on said modules being spaced apart consistent with the spacing of said bores for cooperative interfitting of said posts in said bores.

12. An infant supporting and positioning system for supporting an infant in a selected position, said infant positioning system comprising:

a base;

a plurality of infant supporting and positioning modules, each of said plurality of modules having a body portion positioned against and extending away from said base for aiding in the positioning of an infant;

engagement structure operatively associated with said base and said body of said module, said engagement structure retaining said module in a selected position relative to said base to provide support and restraints for supporting an infant in a desired position; and a skull supporting portion operatively associated with said base, an arcuate recess formed in said skull supporting portion for circumferentially supporting a portion of an infants head, said skull supporting portion and said base having a bore extending therethrough for promoting an infant's breathing when the infant is positioned facing the skull supporting portion.

13. An infant supporting and positioning system for supporting an infant in a selected position, said infant positioning system comprising:

a base;

a plurality of infant supporting and positioning modules, each of said plurality of modules having a body portion positioned against and extending away from said base for aiding in the positioning of an infant;

engagement structure operatively associated with said base and said body of said module, said engagement structure retaining said module in a selected position relative to said base to provide support and restraints for supporting an infant in a desired position;

a skull supporting portion operatively associated with said base, an arcuate recess formed in said skull supporting portion for circumferentially supporting a portion of an infant's head; and wherein said plurality of infant positioning modules includes a head positioning module assembly, said head positioning module assembly including said skull supporting portion having oppositely positioned first and second major faces, said arcuate recess being formed in said first major face for circumferentially supporting a portion of an infant's head, post structure projecting from said second major face of said skull supporting portion, said post structure being configured for resisting rotation of said skull supporting portion and for engagement in corresponding ones of said plurality of bores in said base.

14. An infant supporting and positioning system as recited in claim 13, said head positioning module assembly further comprising a head positioning collar, said head positioning collar having a left module and a right module selectably attachable to said skull supporting portion, said left and right modules comprising said head positioning collar extending around at least a portion of an infant's head.

15. An infant supporting and positioning system as recited in claim 14, further including interfitting extensions protruding from each of said left and right modules, said interfitting extensions fitting together to form a continuous generally arcuate surface on the inside of said head positioning collar.

16. An infant supporting and positioning system for supporting an infant in a selected position, said infant positioning system comprising:

a base;

a plurality of infant supporting and positioning modules, each of said plurality of modules having a body portion positioned against and extending away from said base for aiding in the positioning of an infant;

engagement means operatively associated with said base and said body of said module, said engaging means retaining said module in a selected position relative to said base to provide support and restraints for supporting an infant in a desired position;

said engagement means includes a plurality of bores formed in at least one of said body and said base, at least one post operatively coupled with at least one of said bores and operatively coupled with one of said body and said base such that said modules are arrangeable relative to said base by engaging said post in said bores at selected positions on said base in a confirmation to provide support and restraints for supporting an infant in a desired position; and at least one of said modules is formed of a foam material having a degree of flexibility and resiliency, said body and said at least one post of each of said modules being integrally formed as a unitary component, and a resilient surface covering attached to said body of said module.

17. An infant supporting and positioning system for supporting an infant in a selected position, said infant positioning system comprising:

a base;

a plurality of infant supporting and positioning modules, each of said plurality of modules having a body portion positioned against and extending away from said base for aiding in the positioning of an infant said plurality of modules including at least; a pair of upstanding lateral support modules and an independent leg support module;

engagement means operatively associated with said base and said body of each of said lateral support modules and said independent leg support module said engaging means retaining each of said modules in a selected position relative to said base to provide support and restraints for supporting an infant in a desired position, said engagement means includes a plurality of bores formed in at least one of said body of each of said modules and said base, at least one post operatively coupled with at least one of said bores and operatively coupled with one of said body and said base such that each of said modules are attached to said base by engaging said post in said bores at selected positions relative to said base in a configuration to provide support and restraints for supporting an infant in a desired position; and whereby said lateral support modules are generally positionable on said base with said leg support being aligned between said lateral supports, and each of said plurality of modules being independently, selectively attached to said base for accommodating a variety of infant positions.

* * * * *

UNITED STATES PATENT AND TRADEMARK OFFICE
CERTIFICATE OF CORRECTION

PATENT NO. : 5,524,640

DATED : June 11, 1996

INVENTOR(S) : Stephen P. Lisak, Larry L. Young, Sally B. Whitley

It is certified that error appears in the above-indentified patent and that said Letters Patent is hereby corrected as shown below:

On the title page, item [73], should read as follows:

Assignees: RYDER INTERNATIONAL CORPORATION AND THE
UNIVERSITY OF ALABAMA AT BIRMINGHAM RESEARCH FOUNDATION Column 10, Line 11 "supporting and system" should be
--supporting and positioning system --

Column 12, Lines 17-18 "confirmation" should be -- configuration --.

Signed and Sealed this

Twenty-fourth Day of December, 1996

*Attest:*

BRUCE LEHMAN

*Attesting Officer*   Commissioner of Patents and Trademarks